United States Patent
Iaccino et al.

(10) Patent No.: US 10,280,127 B1
(45) Date of Patent: *May 7, 2019

(54) INTEGRATED GAS TURBINE AND CONVERSION SYSTEM PROCESS

(71) Applicant: ExxonMobil Chemical Patents Inc., Baytown, TX (US)

(72) Inventors: Larry L. Iaccino, Seabrook, TX (US); Romain O. V. Lemoine, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/888,365

(22) Filed: Feb. 5, 2018

(51) Int. Cl.
| | |
|---|---|
| *C07C 5/327* | (2006.01) |
| *C07C 5/32* | (2006.01) |
| *C07C 5/333* | (2006.01) |
| *C07C 5/373* | (2006.01) |
| *B01J 8/06* | (2006.01) |

(52) U.S. Cl.
CPC ............... *C07C 5/373* (2013.01); *B01J 8/067* (2013.01); *B01J 2208/00168* (2013.01); *B01J 2208/065* (2013.01); *C07C 2529/44* (2013.01)

(58) Field of Classification Search
CPC ............ C07C 5/327; C07C 5/32; C07C 5/333
USPC ........................ 585/365, 366, 369, 921, 926
See application file for complete search history.

(56) References Cited

U.S. PATENT DOCUMENTS

| | | | | | |
|---|---|---|---|---|---|
| 2,211,211 | A | * | 8/1940 | Kassel | ..................... B01J 38/12 502/52 |
| 2,438,404 | A | * | 3/1948 | Hetzel | ..................... C07C 5/373 585/366 |

* cited by examiner

*Primary Examiner* — Thuan D Dang

(57) ABSTRACT

An integrated process and system to generate power and convert acyclic C5 feedstock to non-aromatic, cyclic C5 hydrocarbon. A combustion device, such as a turbine, and reactor tubes containing catalyst compound are disclosed. A process involving contacting acyclic C5 feedstock with catalyst composition and obtaining cyclic C5 hydrocarbon is also disclosed.

23 Claims, 5 Drawing Sheets

INTEGRATED GAS TURBINE AND CONVERSION SYSTEM PROCESS

CROSS-REFERENCE TO RELATED APPLICATION

This application is a continuation of U.S. Ser. No. 15/288,403, filed Oct. 7, 2016, which claims priority to U.S. Ser. No. 62/250,674, filed Nov. 4, 2015; also, this application relates to U.S. Ser. No. 62/250,693, filed Nov. 4, 2015.

FIELD OF THE INVENTION

This invention relates to integrated gas turbines and convective heated tube reactors, and their use in a process to generate power and for the conversion of acyclic C5 feedstock to a product comprising cyclic C5 compounds.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. Cyclopentadiene (CPD) is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. Co-production of other cyclic C5's is also desirable. Cyclopentane and cyclopentene can have high value as solvents while cyclopentene may be used as a co-monomer to produce polymers and as a starting material for other high value chemicals.

It would be advantageous to be able to produce cyclic C5 compounds including CPD as the primary product from plentiful C5 feedstock using a catalyst system to produce CPD while minimizing production of light (C4−) byproducts. While lower hydrogen content (for example, cyclics, alkenes, and dialkenes) could be preferred because the reaction endotherm is reduced and thermodynamic constraints on conversion are improved, non-saturates are more expensive than saturate feedstock. Linear C5 skeletal structure is preferred over branched C5 skeletal structures due to both reaction chemistry and the lower value of linear C5 relative to branched C5 (due to octane differences). An abundance of C5 is available from unconventional gas and shale oil as well as reduced use in motor fuels due to stringent emissions requirements. C5 feedstock may also be derived from bio-feeds.

Various catalytic dehydrogenation technologies are currently used to produce mono and diolefins from C3 and C4 alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization which is critical to producing CPD. Pt—Sn/alumina and Pt—Sn/aluminate catalysts exhibit moderate conversion of n-pentane, but such catalyst have poor selectivity and yield to cyclic C5 products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing C6 and higher alkanes to form C6 aromatic rings, they are less effective in converting acyclic C5s to cyclic C5s. These Pt supported on chlorided alumina catalysts exhibit low yields of cyclic C5 and exhibit deactivation within the first two hours of time on stream. Cyclization of C6 and C7 alkanes is aided by the formation of an aromatic ring, which does not occur in C5 cyclization. This effect may be due in part to the much higher heat of formation for CPD, a cyclic $C_5$, as compared to benzene, a cyclic C6, and toluene, a cyclic C7. This is also exhibited by Pt/Ir and Pt/Sn supported on chlorided alumina. Although these alumina catalysts perform both dehydrogenation and cyclization of C6+ species to form C6 aromatic rings, a different catalyst will be needed to convert acyclic C5 to cyclic C5.

Ga-containing ZSM-5 catalysts are used in a process to produce aromatics from light paraffins. A study by Kanazirev et al. showed n-pentane is readily converted over $Ga_2O_3/H$—ZSM-5. See Kanazirev et al., "Conversion of C8 aromatics and n-pentane over $Ga_2O_3/H$—ZSM-5 mechanically mixed catalysts," Catalysis Letters, vol. 9, pp. 35-42, 1991. No production of cyclic C5 was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic C5 and high yield to cracking products. This shows that ZSM-S-based catalysts can convert paraffins to a C6 ring, but not necessarily to produce a C5 ring.

U.S. Pat. No. 5,254,787 (Dessau) introduced the NU-87 catalyst used in the dehydrogenation of paraffins. This catalyst was shown to dehydrogenate C2-C6+ to produce their unsaturated analogs. A distinction between C2-5 and C6+ alkanes was made explicit in this patent: dehydrogenation of C2-5 alkanes produced linear or branched mono-olefins or di-olefins whereas dehydrogenation of C6+ alkanes yielded aromatics. U.S. Pat. No. 5,192,728 (Dessau) involves similar chemistry, but with a tin-containing crystalline microporous material. As with the NU-87 catalyst, C5 dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct. A comparative example was conducted on Pt/Sn-ZSM-5 catalysts at varying temperatures, and is discussed below.

U.S. Pat. Nos. 2,438,398; 2,438,399; 2,438,400; 2,438,401; 2,438,402; 2,438,403; and 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of C5 hydrocarbons over platinum nanocatalysts and in the presence of hydrogen sulfide," *Doklady Chemistry*, vol. 424, pp. 27-30, 200, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic C5 products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3-pentadiene with 80% selectivity to CPD with $H_2S$ at 700° C. High temperature, limited feedstock, and potential of products containing sulfur that would later need scrubbing make this process undesirable.

López et al. in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites including H—ZSM-S. At intermediate temperatures (250-400° C.), they reported efficient hydroisomerization of n-pentane on the Pt-zeolites with no discussion of cyclopentenes formation. It is desirable to avoid this deleterious chemistry as branched C5 do not produce cyclic C5 as efficiently as linear C5, as discussed above.

Li et al. in "Catalytic dehydroisomerization of n-alkanes to isoalkenes," *Journal of Catalysis, vol.* 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic C5 were produced and undesirable skeletal isomerization occurred.

U.S. Pat. No. 5,633,421 discloses a process for dehydrogenating C2-C5 paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic C5 hydrocarbons, which are desirable as feedstock because they are plentiful and low cost.

U.S. Pat. No. 7,536,863 describes a combined cycle wherein part of the gas turbine exhaust gas stream is recycled to the gas turbine and the remainder of the gas turbine exhaust gas stream is expelled from the cycle.

Further, many challenges exist in designing an on-purpose CPD production process. For example, the reaction converting C5 hydrocarbons to CPD is extremely endothermic but is favored by low pressure and high temperature but significant cracking of n-pentane and other C5 hydrocarbons can occur at relatively low temperature (e.g., 450° C.-500° C.). Further challenges include loss of catalyst activity due to coking during the process and further processing needed to remove coke from the catalyst, and the inability to use oxygen-containing gas to directly provide heat input to the reactor without damaging the catalyst.

Hence, there remains a need for a process to convert acyclic C5 feedstock to non-aromatic, cyclic C5 hydrocarbons, particularly cyclopentadiene, preferably at commercial rates and conditions. Further, there is a need for a catalytic process targeted for the production of cyclopentadiene which generates cyclopentadiene in high yield from plentiful C5 feedstocks without excessive production of C4-cracked products and with acceptable catalyst aging properties. Additionally, there is a need for processes and reactor systems for on-purpose CPD production from acyclic C5 hydrocarbons, which address the above-described challenges. Further, there is a need for efficient integrated processes and reactor systems for co-production of power and on-purpose CPD.

SUMMARY OF THE INVENTION

This invention relates to a process for converting acyclic C5 hydrocarbon to cyclic C5 hydrocarbon, including but not limited to, cyclopentadiene ("CPD"), wherein the process comprises:

a) compressing a gas stream comprising oxygen;
b) oxidizing fuel with the compressed gas stream to produce a hot gas stream;
c) providing feedstock comprising acyclic C5 hydrocarbon;
d) contacting the feedstock with catalyst composition in parallel reactor tubes while transferring heat by convection from the hot gas stream to the outer surface of the reactor tube walls; and
e) obtaining reactor effluent comprising cyclic C5 hydrocarbon, wherein the cyclic C5 hydrocarbon comprises cyclopentadiene.

Preferably, the oxidizing of b) may be performed in a turbine, fuel cell, furnace, boiler, excess air burner, fluidized bed, and/or other known combustion device. The fuel may be a solid (e.g., coal), liquid (e.g., fuel oil), gas (e.g., H2, methane, natural gas, etc.), or mixture thereof.

This invention also relates to an integrated process for generating power and converting acyclic C5 hydrocarbon to cyclic C5 hydrocarbon, wherein the process comprises:

a) compressing a gas stream comprising oxygen;
b) burning fuel gas with the compressed gas stream in a turbine to produce turbine power and a turbine exhaust stream;
c) providing feedstock comprising acyclic C5 hydrocarbon;
d) contacting the feedstock with catalyst composition in parallel reactor tubes while transferring heat by convection from the turbine exhaust stream to the outer surface of the reactor tube wall; and
e) obtaining reactor effluent comprising cyclic C5 hydrocarbon, wherein the cyclic C5 hydrocarbon comprises cyclopentadiene.

This invention also relates to an integrated process for generating electricity and converting acyclic C5 hydrocarbon to cyclic C5 hydrocarbon in a convectively heated reactor, wherein the process comprises:

a) compressing a gas stream comprising oxygen;
b) oxidizing fuel gas with the compressed gas stream in a fuel cell to produce electricity and a hot gas stream;
c) providing feedstock comprising acyclic C5 hydrocarbon;

d) contacting the feedstock with catalyst composition in parallel reactor tubes while transferring heat by convection from the hot gas stream to the outer surface of the reactor tube wall; and e) obtaining reactor effluent comprising cyclic C5 hydrocarbon, wherein the cyclic C5 hydrocarbon comprises cyclopentadiene.

This invention also relates to an integrated process for generating steam and converting acyclic C5 hydrocarbon to cyclic C5 hydrocarbon in a convectively heated reactor, wherein the process comprises:

a) compressing a gas stream comprising oxygen;
b) oxidizing fuel gas with the fuel stream in a boiler to produce steam and a hot gas stream;
c) providing feedstock comprising acyclic C5 hydrocarbon;
d) contacting the feedstock with catalyst composition in parallel reactor tubes while transferring heat by convection from the hot gas stream to the outer surface of the reactor tube wall; and
e) obtaining reactor effluent comprising cyclic C5 hydrocarbon, wherein the cyclic C5 hydrocarbon comprises cyclopentadiene.

In one aspect of the invention, the reactor tubes have an inverse temperature profile. In another aspect of the invention, the reactor tubes have an isothermal or substantially isothermal temperature profile.

In another aspect of the invention, the feedstock and the hot gas stream, such as the turbine exhaust stream, flow in the same direction providing a heat flux near the inlet that is greater than the heat flux near the outlet of the reactor tubes.

In yet another aspect of the invention further comprises using the turbine power to i) turn a generator producing electric power and/or ii) turn a compressor.

Still yet another aspect of the invention comprises i) providing two or more pluralities of parallel reactor tube(s), the reactor tubes comprising catalyst composition and ii) providing a rejuvenation gas or a regeneration gas to one or more reactor tube pluralities and, at the same time, providing feedstock comprising acyclic C5 hydrocarbons to a different one or more reactor tube pluralities.

Still another aspect of the invention relates to an integrated conversion system for generating power and converting acyclic C5 hydrocarbon to cyclic C5 hydrocarbon, wherein the integrated conversion system comprises:

a) a compressor for compressing a gas stream comprising oxygen;
b) a vessel for burning fuel with the compressed gas stream in the combustion device to produce a hot gas stream;
c) a feedstock stream comprising acyclic C5 hydrocarbon;
d) parallel reactor tubes comprising catalyst composition; and
e) a reactor effluent stream comprising cyclic C5 hydrocarbon produced by contacting at least a portion of the feedstock with catalyst composition in the parallel reactor tube(s) while transferring heat by convection from the hot gas stream to the outer surface of the reactor tube wall, wherein the cyclic C5 hydrocarbon comprises cyclopentadiene.

Preferably, said vessel is a turbine, fuel cell, furnace, boiler, excess air burner, fluidized bed, and/or other known combustion device.

Still another aspect of the invention relates to an integrated conversion system for generating power and converting acyclic C5 hydrocarbon to cyclic C5 hydrocarbon, wherein the integrated conversion system comprises:

a) a compressor for compressing a gas stream comprising oxygen;
b) a turbine for burning fuel gas with the compressed gas stream in the turbine to produce turbine power, and a turbine exhaust stream;
c) a feedstock stream comprising acyclic C5 hydrocarbon;
d) parallel reactor tubes comprising catalyst composition; and
e) a reactor effluent stream comprising cyclic C5 hydrocarbon produced by contacting at least a portion of the feedstock with catalyst composition in the parallel reactor tube(s) while transferring heat by convection from the turbine exhaust stream to the outer surface of the reactor tube wall, wherein the cyclic C5 hydrocarbon comprises cyclopentadiene.

Another aspect of the invention comprises:
a) a rejuvenation gas stream comprising H2; and
b) a means for contacting the rejuvenation gas with the catalyst composition to remove at least a portion of coke material on the catalyst composition.

Yet still another aspect of the invention comprises:
a) a purge stream comprising an inert gas and a regeneration gas stream comprising an oxidizing material; and
b) a means for i) purging any combustible gas, including feedstock and reactor product, from the reactor tubes and ii) contacting the regeneration gas with the catalyst composition to remove by oxidation at least a portion of coke material on the catalyst composition.

DETAILED DESCRIPTION OF THE INVENTION

Definitions

Figure 1:
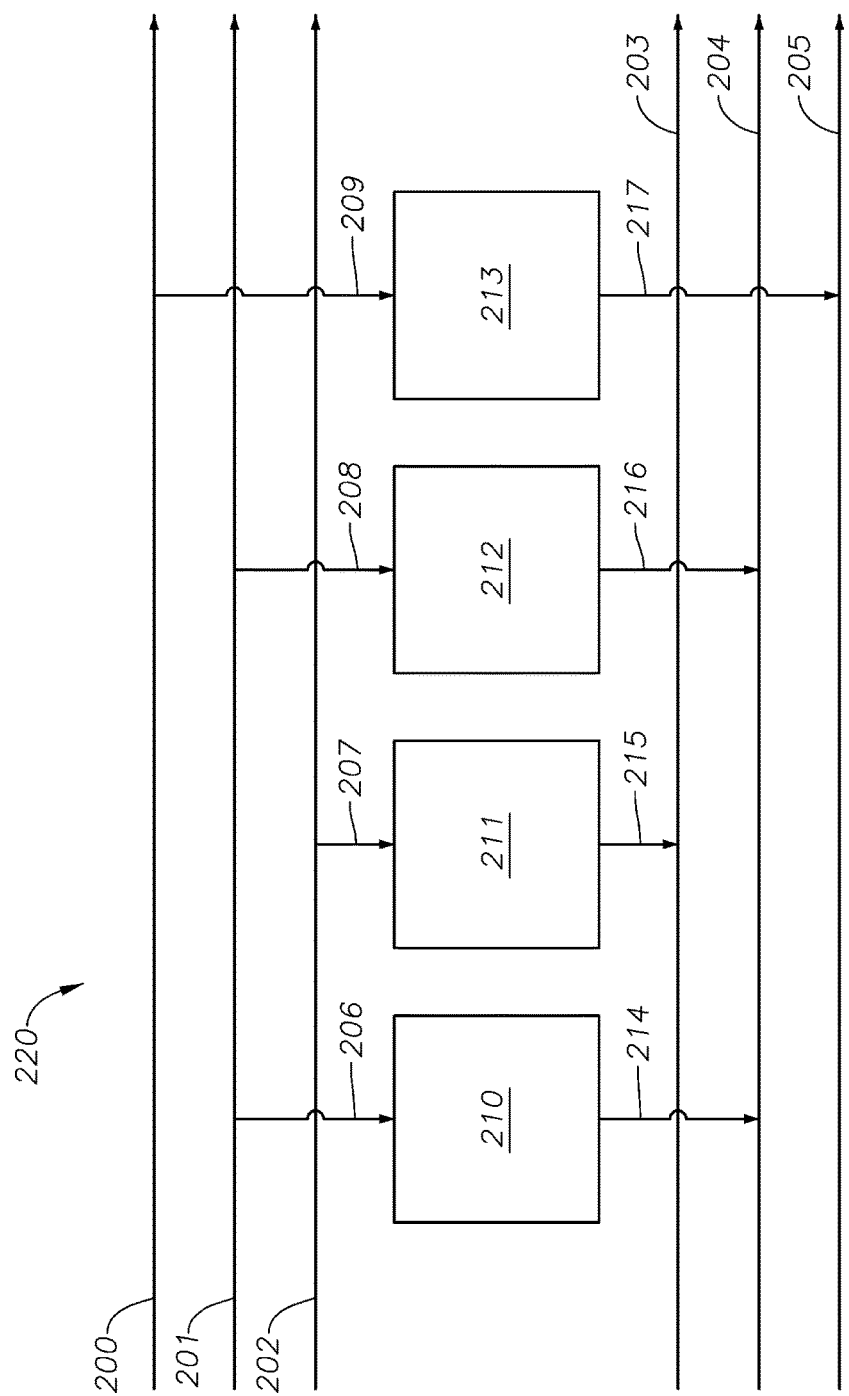
FIG. 1 illustrates an arrangement for multiple reactors.

For the purpose of this specification and the claims thereto, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

As used herein, the term "about" refers to a range of values of plus or minus 10% of a specified value. For example, the phrase "about 200" includes plus or minus 10% of 200, or from 180 to 220.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as benzene. As used herein, the term aromatic encompasses compounds containing one or more aromatic rings, including, but not limited to, benzene, toluene and xylene and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene and xylene and polynuclear aromatics (PNAs), which include naphthalene, anthracene, chrysene, and their alkylated versions.

The term "BTX" includes, but is not limited to, a mixture of benzene, toluene and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "C5 feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

As used herein, the term "oxygen-containing" means oxygen and compounds containing oxygen, including but not limited to O2, CO2, CO, H2O, and oxygen-containing hydrocarbons, such as alcohols, esters, ethers, etc.

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes Ni, Pd, and Pt.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types," Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "carbon selectivity" means the moles of carbon in the respective cyclic C5, CPD, C1, and C2-4 formed divided by total moles of carbon in the pentane converted. The phrase "a carbon selectivity to cyclic C5 of at least 30%" means that 30 moles of carbon in the cyclic C5 is formed per 100 moles of carbon in the pentane converted.

As used herein, the term "conversion" means the moles of carbon in the acyclic C5 feedstock that is converted to a product. The phrase "a conversion of at least 70% of said acyclic C5 feedstock to said product" means that at least 70% of the moles of said acyclic C5 feedstock was converted to a product.

As used herein, the term "reactor system" refers to a system including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and as applicable, reactions zones across multiple reactors. In other words and as is common, a single reactor may have multiple reaction zones. Where the description refers to a first and second reactor, the person of ordinary skill in the art will readily recognize such reference includes two reactors, as well as a single reactor having first and second reaction zones. Likewise, a first reactor effluent and a second reactor effluent will be recognized to include the effluent from the first reaction zone and the second reaction zone of a single reactor, respectively.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

This invention relates to processes for converting acyclic C5 hydrocarbon to cyclic C5 hydrocarbon. In certain aspects, this invention relates to an integrated process for generating power and converting acyclic C5 hydrocarbon to cyclic C5 hydrocarbon, wherein the process comprises: compressing a gas stream comprising oxygen; burning fuel gas with the compressed gas stream in a turbine to produce turbine power and a turbine exhaust stream; providing feedstock comprising acyclic C5 hydrocarbon; contacting the feedstock with catalyst composition in parallel reactor tubes while transferring heat by convection from the turbine exhaust stream to the outer surface of the reactor tube wall; and obtaining reactor effluent comprising cyclic C5 hydrocarbon wherein, the cyclic C5 hydrocarbon comprises cyclopentadiene. Aspects of the conversion system and process enable maintaining an inverse temperature profile in the reactor tubes, which may advantageously minimize carbonaceous material formation and an increase product yield. Other aspects of the invention permit operating the reactor outlet at a sub-atmospheric pressure enhancing formation of cyclic C5 product. Still other aspects of the invention present the advantage of improving overall energy utilization and minimizing energy cost by extracting the highest value heat as shaft work while reducing or eliminating the number of additional combustion devices, e.g., burners, required to heat the conversion process.

Feedstock

Acyclic C5 feedstock useful herein is obtainable from crude oil or natural gas condensate, and can include cracked C5 (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic C5 feedstock useful in the process of this invention comprises pentane, pentene, pentadiene, and mixtures of two or more thereof. Preferably, in one or more embodiments, the acyclic C5 feedstock comprises at least about 50 wt %, or 60 wt %, or 75 wt %, or 90 wt % n-pentane, or in the range from about 50 wt % to about 100 wt % n-pentane.

The acyclic C5 feedstock optionally does not comprise C6 aromatic compounds, such as benzene, preferably C6 aromatic compounds are present at less than 5 wt %, preferably less than 1 wt %, preferably present at less than 0.01 wt %, preferably at 0 wt %.

The acyclic C5 feedstock optionally does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic C5 feedstock optionally does not comprise C6+ aromatic compounds, preferably C6+ aromatic compounds are present at less than 5 wt %, preferably less than 1 wt %, preferably present at less than 0.01 wt %, preferably at 0 wt %.

The acyclic C5 feedstock optionally does not comprise C6+ compounds, preferably C6+ compounds are present at less than 5 wt %, preferably less than 1 wt %, preferably present at less than 0.01 wt %, preferably at 0 wt %.

Preferably, the C5 feedstock is substantially free of oxygen-containing compounds. "Substantially free" used in this context means the feedstock comprises less than about 1.0 wt. %, based upon the weight of the feed, e.g., less than about 0.1 wt. %, less than about 0.01 wt. %, less than about 0.001 wt. %, less than about 0.0001 wt. %, less than about 0.00001 wt. % oxygen-containing compounds.

Preferably, a hydrogen co-feedstock comprising hydrogen and, optionally, light hydrocarbons, such as C1-C4 hydrocarbons, is also fed into the first reactor. Preferably, at least a portion of the hydrogen co-feedstock is admixed with the C5 feedstock prior to being fed into the first reactor. The presence of hydrogen in the feed mixture at the inlet location, where the feed first comes into contact with the catalyst, prevents or reduces the formation of coke on the catalyst particles. C1-C4 hydrocarbons may also be co-fed with the C5.

Acyclic $C_5$ Conversion Process

The first aspect of the invention is a process for conversion of an acyclic C5 feedstock to a product comprising cyclic C5 compounds. The process comprising the steps of contacting said feedstock and, optionally, hydrogen under acyclic C5 conversion conditions in the presence of one or more catalyst compositions, including but not limited to the catalyst compositions described herein, to form said product.

The second aspect of the invention is also a process for conversion of an acyclic C5 feedstock to a product comprising cyclic C5 compounds, the process comprising the steps of contacting said feedstock and, optionally, hydrogen under acyclic C5 conversion conditions in the presence of one or more catalyst compositions, including but not limited to the catalyst compositions described herein, to form said product.

In one or more embodiments, the product of the process for conversion of an acyclic C5 feedstock comprises cyclic C5 compounds. The cyclic C5 compounds comprise one or more of cyclopentane, cyclopentene, cyclopentadiene, and includes mixtures thereof. In one or more embodiments, the cyclic C5 compounds comprise at least about 20 wt %, or 30 wt %, or 40 wt %, or 50 wt % cyclopentadiene, or in the range of from about 10 wt % to about 80 wt %, alternately 10 wt % to 80 wt %.

In one or more embodiments, the acyclic C5 conversion conditions include at least a temperature, a reactor outlet pressure, a reactor pressure drop, and a weight hourly space velocity (WHSV). The temperature is in the range of about 450° C. to about 800° C., or in the range from about 450° C. to about 650° C., preferably, in the range from about 450° C. to about 600° C. The reactor outlet pressure is in the range of about 1 to about 50 psia, or in the range from about 4 to about 25 psia, preferably in the range of about 4 to about 10 psia. Advantageously, operating the reactor outlet at a sub-atmospheric pressure enhances formation of cyclic C5 product. The reactor pressure drop measured from reactor inlet to reactor outlet (reactor inlet pressure—reactor outlet pressure) is in the range of about 1 to about 100 psi, or in the range of from about 1 to about 75 psi, preferably about 5 to about 45 psi. The weight hourly space velocity is in the range from about 1 to about 1000 hr$^{-1}$, or in the range from about 1 to about 100 hr$^{-1}$, preferably from about 2 to about 20 hr$^{-1}$. Such conditions include a molar ratio of the optional hydrogen co-feed to the acyclic C5 feedstock in the range of about 0 to 3, or in the range from about 1 to about 2. Such conditions may also include co-feed C1 to C4 hydrocarbons with the acyclic C5 feed. Preferably co-feed (if present), whether comprising hydrogen, C1-C4 hydrocarbons or both, is substantially free of oxygen-containing compounds. "Substantially free" used in this context means the co-feed comprises less than about 1.0 wt. %, based upon the weight of the co-feed, e.g., less than about 0.1 wt. %, less than about 0.01 wt. %, less than about 0.001 wt. %, less than about 0.0001 wt. %, less than about 0.00001 wt. % oxygen-containing compounds.

In one or more embodiments, this invention relates to a process for conversion of n-pentane to cyclopentadiene comprising the steps of contacting n-pentane and, optionally, hydrogen (if present, typically H$_2$ is present at a ratio to n-pentane of 0.01 to 3.0) with one or more catalyst compositions, including but not limited to the catalyst compositions described herein, to form cyclopentadiene at a reactor outlet temperature of 550° C. to 650° C., a reactor outlet pressure of 4 to about 20 psia, a reactor pressure drop of about 5 to about 45 psi, and a weight hourly space velocity of 2 to about 20 hr$^{-1}$.

Catalyst compositions useful herein include microporous crystalline metallosilicates, such as crystalline aluminosilicates, crystalline ferrosilicates, or other metal containing crystalline silicates (such as those where the metal or metal-containing compound is dispersed within the crystalline silicate structure and may or may not be a part of the crystalline framework. Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11, or 13 metal) greater than about 3, or greater than about 25, or greater than about 50, or greater than about 100, or greater than about 400, or in the range from about 100 to about 2,000, or from about 100 to about 1,500, or from about 50 to about 2,000, or from about 50 to about 1,200.

In one or more embodiments, the crystalline aluminosilicate has an SiO$_2$/Al$_2$O$_3$ molar ratio greater than about 3, or greater than about 25, or greater than about 50, or greater than about 100, or greater than about 400, or in the range from about 100 to about 400, or from about 100 to about 500, or from about 25 to about 2,000, or from about 50 to about 1,500, or from about 100 to about 1,200, or from about 100 to about 1000.

In another embodiment of the invention, the microporous crystalline metallosilicate (such as an aluminosilicate) is combined with a Group 10 metal or metal compound, and, optionally, one, two, three, or more Group 1, 2, or 11 metals or metal compounds.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst composition.

In one or more embodiments, the Group 1 alkali metal includes, or is selected from the group consisting of, Li, Na, K, Rb, Cs, and mixtures of two or more thereof, preferably Na.

In one or more embodiments, the Group 2 alkaline earth metal is selected from the group consisting of Be, Mg, Ca, Sr, Ba, and mixtures of two or more thereof.

In one or more embodiments, the Group 1 alkali metal is present as an oxide and the metal is selected from the group consisting of Li, Na, K, Rb, Cs, and mixtures of two or more thereof. In one or more embodiments, the Group 2 alkaline earth metal is present as an oxide and the metal is selected from the group consisting of Be, magnesium, calcium Sr, Ba, and mixtures of two or more thereof. In one or more embodiments, the Group 1 alkali metal is present as an oxide and the metal is selected from the group consisting of Li, Na, K, Rb, Cs, and mixtures of two or more thereof; and the Group 2 alkaline earth metal is present as an oxide and the metal is selected from the group consisting of Be, magnesium, calcium, Sr, Ba, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition.

In one or more embodiments, the catalyst composition has an Alpha Value (as measured prior to the addition of the Group 10 metal, preferably platinum) of less than about 25, preferably of less than about 15. Alpha Value is determined as described in U.S. Pat. No. 3,354,078; The Journal of Catalysis, v. 4, p. 527 (1965); v. 6, p. 278 (1966); and v. 61, p. 395 (1980) using a constant temperature of 538° C. and a variable flow rate, as described in detail in The Journal of Catalysis, v. 61, p. 395.

In one or more embodiments of aluminosilicates, the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 alkaline earth metal is present as an oxide and the metal is selected from the group consisting of gold, silver, and copper, and mixtures of two or more thereof.

In one or more embodiments, the use of the catalyst compositions of this invention provides a conversion of at least about 70%, or at least about 75%, or at least about 80%, or in the range from about 60% to about 80%, of said acyclic C5 feedstock under acyclic C5 conversion conditions of an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 hr−1.

In one or more embodiments, the use of any one of the catalyst compositions of this invention provides a carbon selectivity to cyclic C5 compounds of at least about 30%, or at least about 40%, or at least about 50%, or in the range from about 30% to about 80%, under acyclic C5 conversion conditions including an n-pentane feedstock with equimolar $H_2$, a temperature in the range of about 550° C. to about 600° C., an-pentane partial pressure between 3 and 10 psia at the reactor inlet, and an n-pentane weight hourly space velocity between 10 and 20 hr−1.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic C5 conversion conditions including an n-pentane feedstock with equimolar $H_2$, a temperature in the range of about 550° C. to about 600° C., an-pentane partial pressure between 3 and 10 psia at the reactor inlet, and an n-pentane weight hourly space velocity between 10 and 20 hr−1.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and more usually, particularly when the composite is prepared in the form of beads, extrudates, pills, oil drop formed particles, spray dried particles, etc., in the range of about 2 to about 80 wt % of the composite.

Catalyst composition shape and design are preferably configured to minimize pressure drop, increase heat transfer, and minimize mass transport phenomena. Catalyst composition may be formed into particles that are randomly loaded into the reactor or may be formed into structured catalyst shapes within the reactor.

Suitable catalyst shape and design are described in WO 2014/053553, which is incorporated by reference in its entirety. The catalyst composition may be an extrudate with a diameter of 2 mm to 20 mm, for example, 2 mm to 10 mm, or 5 mm to 15 mm Optionally, the catalyst composition cross section may be shaped with one or more lobes and/or concave sections. Additionally, the catalyst composition lobe and/or concave sections may be spiraled. The catalyst composition may be an extrudate with a diameter of 2 mm to 20 mm, for example, 2 mm to 10 mm, or 5 mm to 15 mm; and the catalyst composition cross section may be shaped with one or more lobes and/or concave sections; and the catalyst composition lobes and/or concave sections may be spiraled. For fixed bed reactors (fired tube, convective tube, and cyclic) lobed, concave, spiral, etc., particle shapes are particularly useful and for fluid bed reactors spherical particle shapes are particularly useful. Preferably, particles for a fixed bed (e.g., cyclic fixed bed reactor, fired tubes reactor, convectively heated tubes reactor, etc.) are typically an extrudate with a diameter of 2 mm to 20 mm; and the catalyst composition cross section may be shaped with one or more lobes and/or concave sections; and the catalyst composition lobes and/or concave sections may be spiraled. Shapes may also include holes or perforations in the shapes to increase voidage and improve mas transfer.

Structured catalyst shape examples include a coating of catalyst onto the inner wall of the reactor and/or onto other formed inorganic support structures. Suitable formed inorganic support structures may be metallic or ceramic. Preferred ceramics are those with high thermal conductivity, e.g., silicon carbide, aluminum nitride, boron carbide, and silicon nitride. Suitable formed inorganic support structures may be ordered structures, such as extruded ceramic monoliths and extruded or rolled metal monoliths. Often, suitable formed inorganic support structures may also include ceramic or metal foams and 3D printed structures. The coating of active catalyst may be applied to the support structures via wash coating or other means known in the art. Preferably, the coating thickness is less than 1,000 microns; more preferably less than 500 microns; most preferably between 100 and 300 microns.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by techniques, including high pressure hydrogen treatment and combustion of coke on the catalyst compositions with oxygen, such as air or $O_2$ gas.

Useful catalyst compositions comprise a crystalline aluminosilicate or ferrosilicate, which is optionally combined with one, two, or more additional metals or metal compounds. Preferred combinations include:
1) a crystalline aluminosilicate (such as ZSM-5 or Zeolite L) combined with a Group 10 metal (such as Pt), a Group 1 alkali metal (such as sodium or potassium), and/or a Group 2 alkaline earth metal;
2) a crystalline aluminosilicate (such as ZSM-5 or Zeolite L) combined with a Group 10 metal (such as Pt) and a Group 1 alkali metal (such as sodium or potassium);
3) a crystalline aluminosilicate (such as a ferrosilicate or an iron treated ZSM-5) combined with a Group 10 metal (such as Pt) and a Group 1 alkali metal (such as sodium or potassium);
4) a crystalline aluminosilicate (Zeolite L) combined with a Group 10 metal (such as Pt) and a Group 1 alkali metal (such as potassium); and
5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as a Li, Na, K, Rb, and/or Cs silicates) and/or a Group 2 alkaline earth metal silicate (such as e, Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica (SiO2) may be any silica typically used as catalyst support such as those marketed under the tradenames of DAVISIL 646 (Sigma Aldrich), Davison 952, DAVISON 948 or Davison 955 (Davison Chemical Division of W.R. Grace and Company).

In various aspects, the catalyst material (and optional matrix material) may have an average diameter of about 5 μm to about 50 mm, such as about 25 μm to about 3500 μm. Preferably, the catalyst material (and optional matrix or binder) may have an average diameter of about 25 μm to about 1200 μm, more preferably about 50 μm to about 1000 μm, more preferably about 10 μm to about 500 μm, more preferably about 30 μm to about 400 μm, more preferably about 40 μm to about 300 μm.

"Average diameter" for particles in the range of 1 to 3500 μm is determined using a Mastersizer™ 3000 available from Malvern Instruments, Ltd., Worcestershire, England. Unless otherwise stated, particle size is determined at D50. D50 is the value of the particle diameter at 50% in the cumulative distribution. For example, if D50=5.8 um, then 50% of the particles in the sample are equal to or larger than 5.8 um and 50% are smaller than 5.8 um. (In contrast, if D90=5.8 um, then 10% of the particles in the sample are larger than 5.8 um and 90% are smaller than 5.8 um.) "Average diameter" for particles in the range of 3 mm to 50 mm is determined using a micrometer on a representative sample of 100 particles.

For more information on useful catalyst compositions, please see applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015; which are incorporated herein by reference.

Conversion System

The feedstock is fed into the conversion system comprising parallel reactor tube(s) positioned within an enclosure. Optionally, the feedstock is fed to an adiabatic lead reaction zone prior to being fed to the parallel reactor tube(s). For more information on the use of an adiabatic lead reaction zone, please see U.S. Ser. No. 62/250,697, filed Nov. 4, 2015, which is incorporated herein by reference. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. Advantageously, the tubes have a small cross sectional size to minimize cross sectional temperature gradients. However, decreasing the cross sectional size of the tubes increases the number of tubes for a given production rate. Therefore, an optimum tube size selection is preferably optimized with respect to minimizing cross sectional temperature gradient and minimizing cost of construction. Suitable cross sectional sizes (i.e., diameters for the cylindrical tubes) may be from 1 cm to 20 cm, more preferably from 2 cm to 15 cm, and most preferably from 3 cm to 10 cm.

The tubes are heated with a hot gas stream produced by oxidizing fuel with a compressed gas stream comprising oxygen. Often, the tubes are heated with a turbine exhaust stream produced by a turbine burning fuel gas with a compressed gas comprising oxygen. In other aspects, the reactor tubes are heated by convection with hot gas produced by combustion in any known combustion device, wherein the combustion device is preferably selected from a fuel cell, furnace, boiler, or excess air burner. However, heating the reactor tubes with turbine exhaust may be preferred because of the co-production of power or shaft work among other advantages.

The compressed gas comprising oxygen is compressed in at least one compressor. Preferably, the compressed gas is compressed air. Optionally, the compressed gas comprises air enriched in oxygen by partial separation of nitrogen. Any compressor and/or turbine known in the art may be used. Examples of suitable compressors and turbines for use in the conversion system are described in U.S. Pat. No. 7,536,863, which is incorporated herein by reference. Preferably the turbine additionally produces power. The turbine power may be used to turn the compressor that compresses the compressed gas comprising oxygen. Optionally, the conversion system further comprises a generator and/or an additional compressor turned with the power produced by the turbine. The generator may produce electric power.

Heat is transferred by convection from the hot gas stream, often the turbine exhaust stream, to the outer surface of the reactor tube wall. The reactor tubes may be positioned in the enclosure in any configuration. Preferably the reactor tubes are positioned within the enclosure to provide co-current flow of feedstock and the hot gas stream (e.g., the turbine exhaust). Co-current flow provides a heat flux near the reactor tube inlet that is greater than the heat flux near the reactor tube outlet. Higher heating is desired near the reactor tube inlet, e.g., for providing the heat of reaction plus heat required to heat up feedstock to desired reaction temperature. Lower heat flux (relative to the amount of heat flux at the inlet) is desired near an outlet portion of the reactor tube to avoid greater than desired temperatures, e.g., temperatures promoting undesired coking and/or cracking that occurs with temperatures above the desired conversion condition temperature range for a given catalyst, operating pressure, and/or residence time.

The conversion system optionally further comprises at least one combustion device enabling additional heat input into the hot gas stream, such as the turbine exhaust stream. Additional heat may be provided by a combustion device to the hot gas stream (e.g., the turbine exhaust stream) upstream or downstream of the reactor tubes. Additional fuel gas may be burned with unreacted oxygen in the hot gas stream (e.g., the turbine exhaust stream) to increase temperature of the hot gas stream (e.g., the turbine exhaust stream) prior to or subsequent to transferring heat by convection from the hot gas stream (e.g., the turbine exhaust stream) to the reactor tube walls. The additional heat input may be provided to the hot gas stream (e.g., the turbine exhaust stream) by any combustion device known in the art. Examples of suitable combustion devices include a duct burner, supplemental burner, or other device well known for supplemental heating of flue gas.

In certain aspects, the hot gas stream may be at a higher temperature than desired (i.e., the conversion process would be carried out at a higher than desired temperature due to the heat input from the hot gas stream). In such aspects, the temperature of the hot gas stream may be reduced prior to contacting the reactor tubes. Preferred methods of reducing the temperature of the hot gas stream include mixing the hot gas stream with a cooler gas stream (such as additional air and/or recirculated cooled gas) and/or passing the hot gas stream through a heat exchanger. Excess heat from the hot gas stream may preferably be used to provide heat to the conversion process, to preheat the fuel or the gas stream comprising oxygen, and/or to generate steam.

The reactor tubes contain catalyst composition therein. The catalyst composition may be coated on the reactor tube inner surface or may be part of a fixed bed (which includes both random and structured beds) of catalyst within the tubes. Preferably, the reactor tubes contain a fixed bed of catalyst composition and inert material. Suitable methods of packing and or designing fixed beds of reactor tubes include U.S. Pat. No. 8,178,075, which is incorporated entirely by reference. The reactor tubes may include at least one internal structure, e.g., concentric shells, to support the catalyst composition and/or reduce pressure drop within the reactor tube. The reactor tubes may comprise mixing internal structures positioned within the reactor tubes providing mixing in the radial direction. The mixing internal structures may be positioned within a bed of catalyst composition or in portions of the reactor tube separating two or more zones of catalyst composition. The reactor tubes may comprise fins or contours on the inside or outside of the reactor tubes promoting heat transfer from the tube wall to the catalyst composition. The fins or contours may be positioned to provide a heat flux near the inlet that is greater than the heat flux near the outlet of the reactor tubes. Examples of suitable internal structures include a plurality of baffles, sheds, trays, tubes, rods, fins, contours, and/or distributors. These internal structures may be coated with catalyst. Suitable internal structures may be metallic or ceramic. Preferred ceramics are those having high thermal conductivity, e.g., silicon carbide, aluminum nitride, boron carbide, and silicon nitride.

The temperature profile of the reaction zone may be manipulated by controlling the rate of heat input (based on hardware design, catalyst loading, firing, etc.). Notwithstanding providing a heat flux near the inlet that is greater than the heat flux near the reactor tube outlet, a substantially isothermal temperature profile may be provided, measured along the tube centerline. A substantially isothermal temperature profile has the advantages of maximizing the effective utilization of the catalyst and minimizing the production of undesirable C4− byproducts. As used herein, "isothermal temperature profile" means that the temperature at each point between the reactor inlet and reactor outlet as measured along the tube centerline of the reactor is kept essentially constant, e.g., at the same temperature or within the same narrow temperature range wherein the difference between an upper temperature and a lower temperature is no more than about 40° C.; more preferably no more than about 20° C. Preferably, the isothermal temperature profile is one where the reactor inlet temperature is within about 40° C. of the reactor outlet temperature, alternately within about 20° C., alternately within about 10° C., alternately within about 5° C., alternately the reactor inlet temperature is the same as the reactor outlet temperature. Alternately, the isothermal temperature profile is one where the reactor inlet temperature is within about 20% of the reactor outlet temperature, alternately within about 10%, alternately within about 5%, alternately within about 1%.

Preferably, the isothermal temperature profile is one where the temperature along the length of the reaction zone(s) within the reactor does not vary by more than about 40° C. as compared to reactor inlet temperature, alternately not more than about 20° C., alternately not more than about 10° C., alternately not more than about 5° C. Alternately, the isothermal temperature profile is one where the temperature along the length of the reaction zone(s) within the reactor is within about 20% of the reactor inlet temperature, alternately within about 10%, alternately within about 5%, alternately within about 1% of the reactor inlet temperature.

However, to minimize catalyst deactivation rate it may be preferable to optimize the conversion system design so a substantially inverse temperature profile is maintained in the tubular reactor. As used herein, "inverse temperature profile" means that the reactor inlet temperature is lower than the reactor outlet temperature. Preferably, tube centerline temperature at the tube inlet is lower than the tube centerline temperature at the tube outlet. "Inverse temperature profile" includes systems where the temperature varies in the reactor or systems so long as the temperature at the reactor inlet is lower than the temperature at the reactor outlet. "Inverse temperature profile" further encompasses a reactor tube having a centerline temperature T1; at some length along the reactor tube, the centerline temperature decreases to temperature T2; at a further length along the reactor tube, the centerline temperature rises to temperature T3; finally, the centerline temperature at the reactor tube outlet decreases to temperature T4; wherein T3>T4>T1>T2.

The temperature measured where feedstock first contacts catalyst composition near the reactor inlet may be between about 0° C. to about 200° C., preferably, about 25° C. to about 150° C., more preferably about 50° C. to about 100° C., lower than the temperature measured where the effluent leaves contact with catalyst composition near the reactor outlet. Preferably, the tube centerline temperature measured where feedstock first contacts catalyst composition near the tube inlet may be between about 0° C. to about 200° C., preferably, about 25° C. to about 150° C., more preferably about 50° C. to about 100° C., lower than the tube centerline temperature measured where the effluent leaves contact with catalyst composition near the tube outlet.

Maintaining an inverse temperature profile in the reactor tube may advantageously minimize carbonaceous material formation at the inlet, which can contribute to coking of the catalyst composition. The inverse temperature profile may also provide sufficient reaction time and length in the reactor tube to produce a sufficient amount of $H_2$, at lower operating temperatures than outlet temperature, which can minimize carbonaceous material formation at the outlet for an effluent.

The conversion system may further comprise heat transfer means for transferring an additional amount of heat by convection from the hot gas stream (e.g., the turbine exhaust) to other streams such as a rejuvenation gas, a regeneration gas, the feedstock (before the feedstock enters the reactor tubes), the fuel (e.g., the fuel gas), the gas stream comprising oxygen, and/or steam. The additional heat transfer means may be any suitable means of heat transfer known in the art. Suitable heat transfer means include heat exchanger tube bundles. The heat transfer means may be positioned in the reactor tube enclosure so that additional heat is transferred from the hot gas stream (e.g., the turbine exhaust) before or after heat is transferred to the reactor tubes from the hot gas stream (e.g., the turbine exhaust).

The conversion system may further comprise two or more pluralities of parallel reactor tubes within convective heat transfer enclosure(s). The conversion system may comprise two or more enclosures, each enclosure comprising a plurality of parallel reactor tubes containing catalyst composition. The conversion system may also comprise means for controlling flow of the hot gas stream (e.g., the turbine exhaust) to each plurality. Suitable flow control means include control valves, baffles, louvres, dampers, and/or conduits. The conversion system may also include capability to divert at least a portion of the hot gas stream (e.g., the turbine exhaust) away from or around the reactor tubes and conduct the hot gas stream (e.g., the turbine exhaust) to other heat recovery devices or to an exhaust stack. The conversion system may also include auxiliary equipment such as exhaust gas silencers and scrubbers.

Rejuvenation

During the conversion process, carbonaceous or coke material forms on the catalyst composition, reducing the activity of the catalyst composition. The amount of coke that is deposited on the catalysts during a conversion cycle is referred to as the incrementally deposited coke. A rejuvenation cycle is used to remove at least a portion of the incrementally deposited coke material from the catalyst composition. Rejuvenation begins by discontinuing flow of acyclic C5 feedstock to the reactor tubes and reducing the amount of heat transferred by convection from the hot gas stream (e.g., the turbine exhaust). The amount of heat transferred to the reactor tubes from the hot gas stream (e.g., the turbine exhaust stream) may be reduced by limiting the flow of the hot gas stream (e.g., the turbine exhaust stream) and/or diverting a portion of the hot gas stream (e.g., the turbine exhaust stream) away from the reactor tubes. A rejuvenation gas substantially free of reactive oxygen-containing compounds and comprising hydrogen ($H_2$) is provided to the reactor tubes. "Substantially free" used in this context means the rejuvenation gas comprises less than about 1.0 wt. %, based upon the weight of the rejuvenation gas, e.g., less than about 0.1 wt. %, less than about 0.01 wt. %, less than about 0.001 wt. %, less than about 0.0001 wt. %, less than about 0.00001 wt. % oxygen-containing compounds. "Reactive oxygen-containing compounds" are compounds where the oxygen is available to react with the catalyst as compared to inert compounds containing oxygen (such as CO) which do not react with the catalyst.

Flow of rejuvenation gas may be in the same or opposite direction to the discontinued feedstock flow. The rejuvenation gas comprises ≥50 wt % $H_2$, such as ≥60 wt %, ≥70 wt %, preferably ≥90 wt % $H_2$. Rejuvenation gas may further comprise an inert substance (e.g., $N_2$, CO), and/or methane.

The rejuvenation gas is contacted with the catalyst composition inside the reactor tube forming light hydrocarbon and removing at least 10 wt % (>10 wt %) of incrementally deposited coke material. Between about 10 wt % to about 100 wt %, preferably between about 90 wt % to about 100 wt % of incrementally deposited coke material is removed. Following coke material removal, flow of rejuvenation gas is halted and acyclic C5 feedstock flow, as well as increased amount of heat transfer by convection from the hot gas stream (e.g., the turbine exhaust) is resumed.

Rejuvenation in the specified conversion system advantageously has a time duration of ≤90 mins, e.g., ≤60 mins, ≤30 mins, ≤10 mins, such as ≤1 min, or ≤10 seconds. Contacting catalyst composition with the rejuvenation gas occurs at a temperature of about 500° C. to about 900° C., preferably about 575° C. to about 750° C. The reactor tube outlet pressure is between about 5 psia to about 250 psia, preferably about 25 psia to about 250 psia during rejuvenation cycle. Rejuvenation may be advantageously performed ≥10 minutes, e.g., ≥30 minutes, ≥2 hours, ≥5 hours, ≥24 hours, ≥2 days, ≥5 days, ≥20 days, after beginning the specified conversion process.

Rejuvenation effluent exiting the reactor tubes and comprising light hydrocarbon, unreacted hydrogen, and coke particulate may be sent to a compression device and then sent to a separation apparatus wherein a light hydrocarbon enriched gas and light hydrocarbon depleted gas is produced. The light hydrocarbon gas may be carried away, e.g., for use as fuel gas. The light hydrocarbon depleted stream may be combined with make-up hydrogen and make up at least a portion of the rejuvenation gas provided to the reactor tubes. The separation apparatus may be a membrane system, adsorption system (e.g., pressure swing and/or temperature swing), or other known system for separation of hydrogen from light hydrocarbons. A particulate separation device, e.g., a cyclonic separation drum, may be provided wherein coke particulate is separated from the effluent rejuvenation gas.

Regeneration

During the conversion process, some carbonaceous or coke material forms on the catalyst composition that is not removed by oxygen free rejuvenation with $H_2$ containing rejuvenation gas. An oxidative regeneration is used to remove at least a portion of this coke material from the catalyst composition. The regeneration cycle begins by discontinuing flow of feedstock to the reactor tubes and reducing the amount of heat transferred by convection from the hot gas stream (e.g., the turbine exhaust). Combustible hydrocarbon gas, including feedstock or reactor product (acyclic and cyclic C5 hydrocarbon), is purged from the reactor tubes using a purge gas, for example, N2. Following hydrocarbon purging, a regeneration gas comprising an oxidizing material such as oxygen, for example, air, is provided to the reactor tubes. Regeneration gas is contacted with the catalyst composition inside the reactor tube to remove by oxidation at least 10 wt % (≥10 wt %) of coke material present at the start of regeneration. Between about 10 wt % to about 100 wt %, preferably between about 90 wt % to about 100 wt % of coke material is removed. Following coke material removal, flow of rejuvenation gas is halted and purge gas is reintroduced to purge oxygen-containing regeneration gas from the reactor tubes. Subsequent to purging oxygen, flow of acyclic C5 feedstock may be resumed, along with increased amount of heat transfer by convection from the hot gas stream (e.g., the turbine exhaust).

Regeneration, including purging before and after coke oxidation, requires less than about 10 days, preferably less than about 3 days to complete. Regeneration may be performed between about once every 6 days to about once every 180 days, preferably between about once every 10 days to about once every 40 days.

Multiple Enclosure Arrangement

The conversion system may further comprise two or more pluralities of parallel reactor tubes within convective heat transfer enclosure(s). The conversion system may comprise two or more enclosures, each enclosure comprising a plurality of parallel reactor tubes containing catalyst composition. The conversion system may also comprise means for controlling flow of the hot gas stream (e.g., the turbine exhaust) to each plurality. Suitable flow control means include control valves, baffles, louvres, dampers, and/or conduits.

The conversion process of the specified conversion system can comprise providing a rejuvenation gas or a regeneration gas to one or more pluralities of reactor tubes and, at the same time, providing feedstock comprising acyclic C5 hydrocarbon to a different one or more reactor tube pluralities.

FIG. 1 illustrates one possible arrangement 220 for multiple reactors (reactor tube pluralities) interconnected in parallel. Feedstock comprising C5 hydrocarbons (e.g., acyclic C5 hydrocarbons) may be distributed to all the reactors from one feedstock header 201 (not all conduits from every header to every reactor are shown in FIG. 1.). Product may be collected from all the reactors via one product header 204. For information on possible dispositions of the collected product, please see applications:

1) U.S. Ser. No. 62/250,678, filed Nov. 4, 2015;
2) U.S. Ser. No. 62/250,692, filed Nov. 4, 2015;
3) U.S. Ser. No. 62/250,702, filed Nov. 4, 2015; and
4) U.S. Ser. No. 62/250,708, filed Nov. 4, 2015;
which are incorporated herein by reference.

Similarly, there may be one rejuvenation gas supply header 202 for the rejuvenation gas and/or one regeneration gas supply header 200 for regeneration gas that is distributed to all the reactors. A regeneration effluent header 205 may collect regeneration effluent from all the reactors. Likewise, a rejuvenation effluent header 203 may collect rejuvenation effluent from all the reactors. While an arrangement of four (4) reactors is shown in FIG. 1, the invention is not limited by this number. Arrangements of multiple reactors having 2, 3, 4, 5, 6, 7, 8, 9, 10, or more reactors are suitable for the invention. Preferable is a multiple reactor arrangement having five (5) reactors.

Feedstock comprising acyclic Cs may be provided from feedstock header 201 to at least one reactor, e.g., via conduit 206 to reactor 210 and/or via conduit 208 to reactor 212, as part of the "on oil" conversion cycle. Reactor effluent comprising cyclic C5 product exiting the "on-oil" reactors (e.g., via conduits 214 and/or 216) is combined and conducted away via common product header 204. Concurrent to the "on-oil" conversion, rejuvenation gas may be provided to one or more reactors, e.g., via conduit 207 to reactor 211. Similarly, regeneration gas and purge gas may be provided concurrently to one or more reactors through regeneration gas supply header 200, e.g., via conduit 209 to reactor 213. Regeneration effluent may be collected from the one or more reactors provided regeneration gas and purge gas. For example, regeneration effluent may be collected from reactor 213 via conduit 217 to regeneration effluent header 205. Rejuvenation effluent may be collected from the one or more reactors provided rejuvenation gas. For example, rejuvenation effluent may be collected from reactor 211 via conduit 215 to rejuvenation effluent header 203. Each reactor is designed with valving systems not shown to enable connection to and isolation from all the various headers dependent on whether the reactor is in use for on-oil feedstock conversion, rejuvenation, and/or regeneration cycles. The figure indicates flows at a specific point in time. It should be recognized that at other points in time the flows may depart from those shown in the figure, as reactors may periodically be exposed to on-oil feedstock conversion, rejuvenation, and/or regeneration cycles. Any valving system and control system known in the art may be used, e.g., double block and bleed to prevent contacting of flammable gases and oxidant gases.

Advantageously, the conversion process can comprise a cyclic arrangement for concurrent "on-oil" feedstock conversion, rejuvenation, and/or regeneration in a multiple reactor conversion system. "On-oil" conversion time is typically greater than 10 minutes, often from about 10 minutes to about 20 days. Rejuvenation time is typically from about 10 seconds to about 2 hours. The arrangement 220 indicated in FIG. 1 allows multiple reactors, e.g., reactors 210, 211, and 212, may repeat a rotating cycle "on-oil" conversion and rejuvenation, while at least one other reactor, e.g., reactor 213, completes regeneration. When regeneration of a reactor, e.g., reactor 213, is complete, it may be returned to "on-oil" conversion/rejuvenation cycle, while another reactor, e.g., reactor 210, may be cycled out for regeneration as required. Advantageously, such an arrangement provides more consistent product composition while reducing the amount of equipment needed.

FURTHER EMBODIMENTS

This invention further relates to:

Embodiment 1

An integrated process for generating power and converting acyclic C5 hydrocarbon to cyclic C5 hydrocarbon, wherein the process comprises:
a) compressing a gas stream comprising oxygen;
b) burning fuel gas with the compressed gas stream in a turbine to produce turbine power and a turbine exhaust stream;
c) providing feedstock comprising acyclic C5 hydrocarbon;
d) contacting the feedstock with catalyst composition in parallel reactor tubes while transferring heat from the turbine exhaust stream to the outer surface of the reactor tube wall;
and
e) obtaining reactor effluent comprising cyclic C5 hydrocarbon wherein, the cyclic C5 hydrocarbon comprises cyclopentadiene.

Embodiment 2

The process of Embodiment 1, wherein the reactor tubes have an inverse temperature profile.

Embodiment 3

The process of Embodiment 1 or 2, wherein the feedstock and the turbine exhaust stream flow in the same direction providing a heat flux at the inlet that is greater than the heat flux at the outlet of the reactor tubes.

Embodiment 4

The process of any of Embodiments 1 to 3, further comprising using the turbine power to i) turn a generator producing electric power and/or ii) turn a compressor.

Embodiment 5

The process of any of Embodiments 1 to 4, further comprising burning additional fuel gas with unreacted oxygen in the turbine exhaust stream to increase the temperature of the turbine exhaust stream prior to said transferring heat by convection in step d).

Embodiment 6

The process of any of Embodiments 1 to 5, wherein the contacting feedstock and catalyst composition is performed in the presence of H2, C1, C2, C3, and/or C4 hydrocarbons.

Embodiment 7

The process of any of Embodiments 1 to 6, further comprising promoting heat transfer to the catalyst composition by providing fins or contours on the inside and/or outside of the reactor tubes.

Embodiment 8

The process of Embodiment 7, wherein the fins and/or the contours promote a heat flux at the inlet that is greater than the heat flux at the reactor tube outlet.

Embodiment 9

The process of any of Embodiments 1 to 8, further comprising mixing feedstock and converted cyclic C5 hydrocarbon in the radial direction by providing mixing internals within the reactor tubes, wherein the mixing internals are positioned i) within a bed of the catalyst composition or ii) in portions of the reactor tube separating two or more zones of catalyst composition.

Embodiment 10

The process of any of Embodiments 1 to 9, wherein contacting feedstock and catalyst composition occurs at a temperature of about 450° C. to about 800° C.

Embodiment 11

The process of any of Embodiments 1 to 10, wherein the feedstock provided to the reactor tubes has a temperature of about 450° C. to about 550° C. at the reactor inlet.

Embodiment 12

The process of any of Embodiments 1 to 11, wherein the reactor tubes have an outlet pressure of about 4 psia to about 50 psia during contacting feedstock.

Embodiment 13

The process of any of Embodiments 1 to 12, wherein the reactor tubes have a pressure drop measured from reactor inlet to reactor outlet from about 1 psi to about 100 psi during contacting feedstock.

Embodiment 14

The process of any of Embodiments 1 to 13, wherein at least about 30 wt % of the acyclic C5 hydrocarbons is converted to cyclopentadiene.

Embodiment 15

The process of any of Embodiments 1 to 14, wherein the catalyst composition comprises platinum on ZSM-5, platinum on zeolite L, and/or platinum on silicate modified silica.

Embodiment 16

The process of Embodiment 15, wherein the catalyst composition further comprises an inert material.

Embodiment 17

The process of any of Embodiments 1 to 16, wherein the catalyst composition is an extrudate having a diameter 2 mm to 20 mm Embodiment 18. The process of any of Embodiments 1 to 17, wherein the catalyst composition cross section is shaped with one or more lobes and/or concave sections.

Embodiment 19

The process of Embodiment 18, wherein the catalyst composition lobes and/or concave sections are spiraled.

Embodiment 20

The process of any of Embodiments 1 to 19, wherein the weight hourly space velocity based on active catalyst content in the reactor tubes is from 1 to 1000 $hr^{-1}$.

Embodiment 21

The process of any of Embodiments 1 to 20, wherein the inside diameter of the reactor tubes is from about 20 mm to about 200 mm.

Embodiment 22

The process of any of Embodiments 1 to 21, wherein i) the feedstock, a regeneration gas, or a rejuvenation gas is conducted to and from the reactor tubes through inlet and outlet manifolds.

Embodiment 23

The process of any of Embodiments 1 to 22, further comprising transferring an additional amount of heat by convection from the turbine exhaust to rejuvenation gas, regeneration gas, the feedstock, the fuel gas, the gas stream comprising oxygen, and/or steam.

Embodiment 24

The process of any of Embodiments 1 to 23, further comprising i) providing two or more pluralities of parallel reactor tube(s), the reactor tubes comprising catalyst composition and ii) providing a rejuvenation gas or a regeneration gas to one or more reactor tube pluralities and, at the same time, providing feedstock comprising acyclic C5 hydrocarbons to a different one or more reactor tube pluralities.

Embodiment 25

The process of any of Embodiments 1 to 24, further comprising:
a) discontinuing providing a feedstock comprising acyclic C5 hydrocarbons and reducing the amount of heat transferred by convection from the turbine exhaust;
b) providing a rejuvenation gas comprising H2;
c) contacting the rejuvenation gas with the catalyst composition to remove at least a portion of coke material on the catalyst composition; and
d) discontinuing providing a rejuvenation gas and resuming providing a feedstock comprising acyclic C5 hydrocarbons and increasing the amount of heat transferred by convection from the turbine exhaust.

Embodiment 26

The process of Embodiment 25, wherein the time duration of steps a) through d) is 1.5 hours or less.

Embodiment 27

The process of Embodiments 25 or 26, wherein contacting rejuvenation gas occurs at a temperature of about 500° C. to about 900° C.

Embodiment 28

The process of any of Embodiments 25 to 27, wherein the reactor tubes have an outlet pressure of about 5 psia to about 250 psia while contacting rejuvenation gas.

Embodiment 29

The process of Embodiments 25 or 26, wherein contacting rejuvenation gas occurs at a temperature of about 575° C. to about 750° C.

Embodiment 30

The process of any of Embodiments 25, 26, or 29, wherein the reactor tubes have an outlet pressure of about 25 psia to about 250 psia, while contacting rejuvenation gas.

Embodiment 31

The process of any of Embodiments 25 to 30, wherein the coke is incrementally deposited and at least 10 wt % of the incrementally deposited coke material is removed from the catalyst composition.

Embodiment 32

The process of any of Embodiments 1 to 31 further comprising:
a) discontinuing providing a feedstock comprising acyclic C5 hydrocarbons and reducing the amount of heat transferred by convection from the turbine exhaust;
b) purging any combustible gas, including feedstock and reactor product, from the reactor tubes;
c) contacting a regeneration gas comprising an oxidizing material with the catalyst composition to remove by oxidation at least a portion of coke material on the catalyst composition;
d) purging regeneration gas from the reactor tubes; and
e) discontinuing purging with regeneration gas and resuming providing a feedstock comprising acyclic C5 hydrocarbons and increasing the amount of heat transferred by convection from the turbine exhaust.

Embodiment 33

An integrated conversion system for generating power and converting acyclic C5 hydrocarbon to cyclic C5 hydrocarbon, wherein the system comprises:
a) a compressor for compressing a gas stream comprising oxygen;
b) a turbine for burning fuel gas with the compressed gas stream in the turbine to produce turbine power and a turbine exhaust stream;
c) a feedstock stream comprising acyclic C5 hydrocarbon;
d) parallel reactor tubes comprising catalyst composition; and
e) a reactor effluent stream comprising cyclic C5 hydrocarbon produced by contacting at least a portion of the feedstock with catalyst composition in the parallel reactor tube(s) while transferring heat, preferably by convection, from the turbine exhaust stream to the outer surface of the reactor tube wall, wherein the cyclic C5 hydrocarbon comprises cyclopentadiene.

Embodiment 34

The system of Embodiment 33, wherein the reactor tubes have an inverse temperature profile.

Embodiment 35

The system of Embodiments 33 or 34, wherein the feedstock and the turbine exhaust stream flow in the same direction providing a heat flux at the inlet that is greater than the heat flux at the outlet of the reactor tubes.

Embodiment 36

The system of any of Embodiments 33 to 35, further comprising at least one combustion device enabling additional heat input into the turbine exhaust stream.

Embodiment 37

The system of any of Embodiments 33 to 36, further comprising fins or contours on the inside or outside of the reactor tubes promoting heat transfer to the catalyst composition.

Embodiment 38

The system of any of Embodiments 33 to 37, further comprising mixing internals positioned within the reactor tubes providing mixing in the radial direction, wherein the mixing internals are positioned i) within a bed of the catalyst composition or ii) in portions of the reactor tube separating two or more zones of catalyst composition.

Embodiment 39

The system of any of Embodiments 33 to 38, wherein the catalyst composition comprises platinum on ZSM-5, platinum on zeolite L, and/or platinum on silicate modified silica.

Embodiment 40

The system of Embodiment 39, wherein the catalyst composition further comprises an inert material.

Embodiment 41

The system of any of Embodiments 33 to 40, wherein the catalyst composition is an extrudate with a diameter of 2 mm to 20 mm Embodiment 42. The system of any of Embodiments 33 to 41, wherein the catalyst composition cross section is shaped with one or more lobes and/or concave sections.

Embodiment 43

The system of Embodiment 42, wherein the catalyst composition lobes and/or concave sections are spiraled.

Embodiment 44

The system of any of Embodiments 33 to 43, wherein the diameter of the reactor tubes is from about 20 mm to about 200 mm.

Embodiment 45

The system of any of Embodiments 33 to 44, further comprising inlet and outlet manifolds in fluid communication with the reactor tubes wherein the feedstock, a regeneration gas, or a rejuvenation gas is conducted to and from the reactor tubes through the inlet and outlet manifolds.

Embodiment 46

The system of any of Embodiments 33 to 45, further comprising heat transfer means for transferring an additional amount of heat by convection from the turbine exhaust to rejuvenation gas, regeneration gas, the feedstock, the fuel gas, the gas stream comprising oxygen, and/or steam.

Embodiment 47

The system of any of Embodiments 33 to 46, further comprising a generator for producing electric power and/or a compressor wherein the generator and/or compressor are/is turned with the turbine power.

Embodiment 48

The system of any of Embodiments 33 to 47, further comprising i) two or more pluralities of parallel reactor tube(s), the reactor tubes comprising catalyst composition and ii) a rejuvenation gas stream or a regeneration gas stream provided to one or more reactor tube pluralities wherein feedstock comprising acyclic C5 hydrocarbons is provided concurrently to a different one or more reactor tube pluralities.

Embodiment 49

The system of any of Embodiments 33 to 48, further comprising:

a) a rejuvenation gas stream comprising H$_2$; and
b) a means for contacting the rejuvenation gas with the catalyst composition to remove at least a portion of coke material on the catalyst composition.

Embodiment 50

The system of any of Embodiments 33 to 49, further comprising:
a) a purge stream comprising an inert gas and a regeneration gas stream comprising an oxidizing material; and
b) a means for i) purging any combustible gas, including feedstock and reactor product, from the reactor tubes and ii) contacting the regeneration gas with the catalyst composition to remove by oxidation at least a portion of coke material on the catalyst composition.

INDUSTRIAL APPLICABILITY

The first hydrocarbon reactor effluent obtained during the acyclic C5 conversion process containing cyclic, branched, and linear C5 hydrocarbons and, optionally, containing any combination of hydrogen, C4 and lighter byproducts, or C6 and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

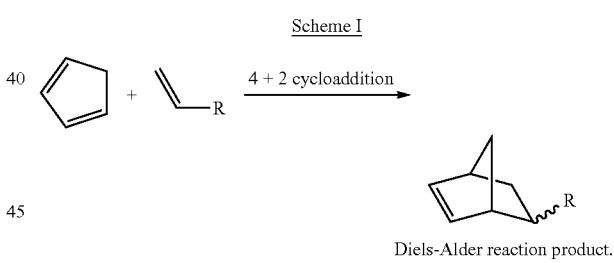

Diels-Alder reaction product.

where R is a heteroatom or substituted heteroatom, substituted or unsubstituted C1-C50 hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

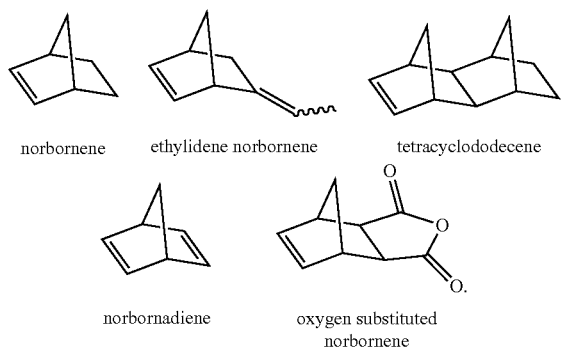

norbornene  ethylidene norbornene  tetracyclododecene norbornadiene  oxygen substituted norbornene The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

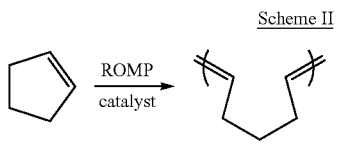

Separated cyclopentane is useful as a blowing agent and as a solvent. Linear and branched C5 products are useful for conversion to higher olefins and alcohols. Cyclic and non-cyclic C5 products, optionally after hydrogenation, are useful as octane enhancers and transportation fuel blend components.

EXAMPLES

The following examples illustrate the present invention. Numerous modifications and variations are possible and it is to be understood that within the scope of the appended claims, the invention may be practiced otherwise than as specifically described herein.

Example 1

Figure 2:
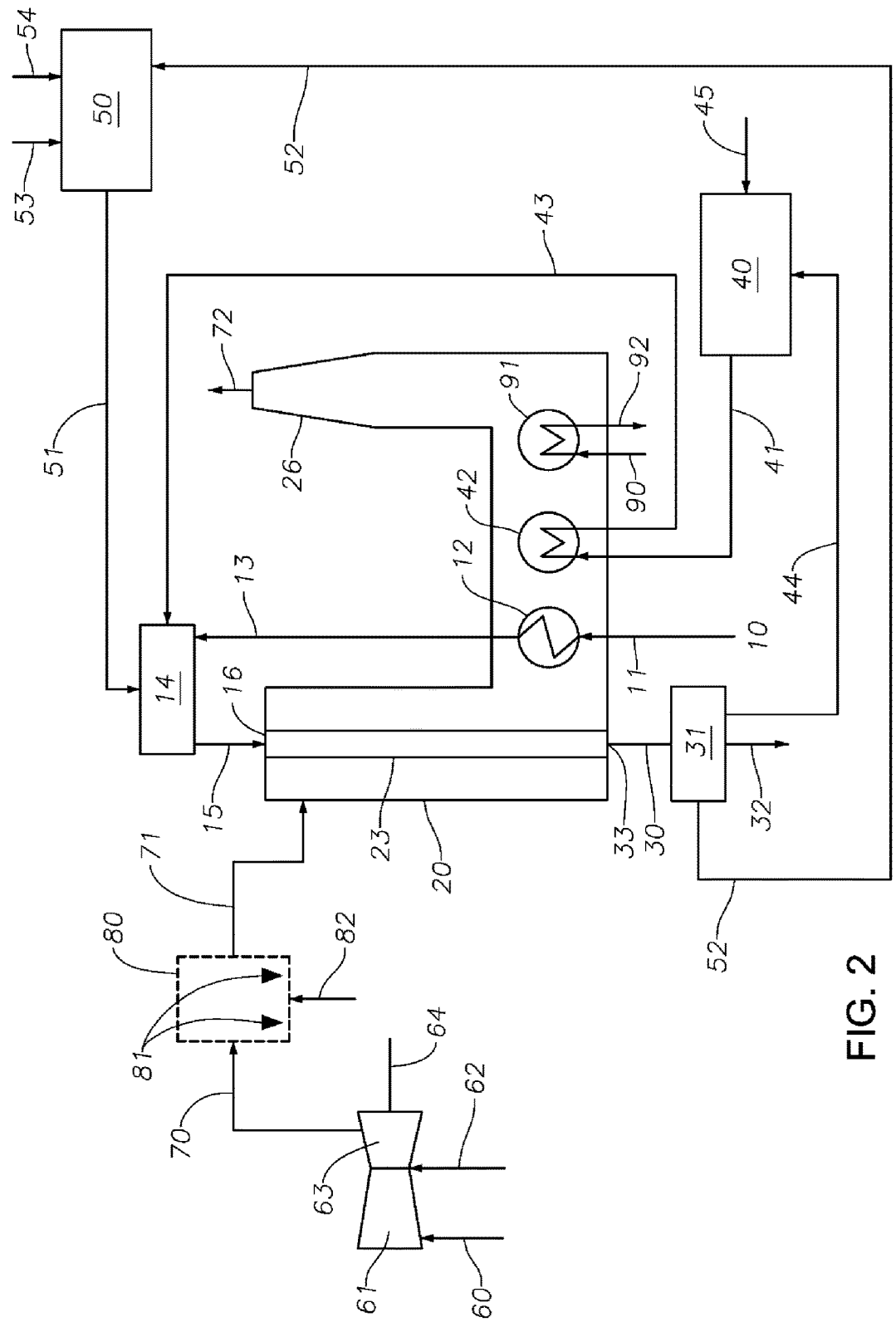
FIG. 2 is a diagram of a conversion system and process.

Referring to FIG. 2, a feedstock 10 comprising acyclic C5 hydrocarbon is provided to parallel reactor tube(s) 23 in enclosure 20. The feedstock is contacted with catalyst composition (not shown) inside reactor tube(s) 23. A reactor effluent 32 comprising cyclic C5 hydrocarbon (e.g., cyclopentadiene) is conducted away as a product or for further processing.

A gas stream 60 comprising oxygen is compressed in compressor 61. Fuel gas 62 is combined with compressed gas in the compressor 61 and burned in turbine 63 producing turbine power 64 and turbine exhaust stream 70. Optionally, additional fuel gas 82 is supplied to additional combustion devices 81 in enclosure 80 where the additional fuel gas 82 is burned with unreacted oxygen in the turbine exhaust stream increasing the temperature of the turbine exhaust stream. Turbine power 64 is used to turn compressor 61 and to turn a generator (not shown) producing electric power.

At least a portion of turbine exhaust stream 70 is conducted to enclosure 20 via conduit 71 where heat is transferred by convection from turbine exhaust stream 70 to the outer surface of the reactor tube(s) 23 walls. Feedstock 10 and turbine exhaust stream 70 flow in the same direction inside enclosure 20 providing higher heat flux near the inlet of reactor tube(s) 23 and lower heat flux near the outlet of reactor tube(s) 23. Reactor tube(s) 23 have an inverse temperature profile. The temperature and flow rate of turbine exhaust stream 70 conducted to enclosure 20 is controlled based on the desired reactor effluent 32 temperature leaving reactor tube(s) 23.

An additional amount of heat is transferred by convection from turbine exhaust stream 70 within enclosure 20 to heat i) the feedstock 10 in exchanger 12, ii) rejuvenation gas 41 in exchanger 42, and iii) steam 90 in exchanger 91. Additional exchangers (not shown) optionally transfer turbine exhaust heat to fuel gas 62, regeneration gas 53, and/or the oxygen-containing gas stream 60. Heated steam produced in exchanger 91 is conducted away via conduit 92 for, inter alia, further use as a utility stream. Cooled exhaust stream 72 is conducted away from enclosure 20 via conduit 26.

Feedstock 10 is conducted via conduit 11 to exchanger 12 and is preheated to about 450° C. to about 550° C. and conducted from exchanger 12 to reactor tube(s) 23 via conduit 13, inlet manifold 14, and conduit 15. The feedstock 10 is contacted with catalyst composition (not shown) at about 450° C. to about 800° C. in reactor tube(s) 23. The outlet pressure of the reactor tube(s) 23 is maintained between about 4 psia to about 50 psia during contacting. Feedstock 10 and converted cyclic C5 hydrocarbon (e.g., cyclopentadiene) are mixed in the radial direction by mixing internals (not shown) inside the reactor tube(s) 23. At least about 30 wt % of the acyclic C5 hydrocarbons in feedstock 10 is converted to cyclopentadiene. The pressure drop across the reactor tube(s) 23 measured from the reactor inlet 16 to the reactor outlet 33 is about 1 psi to about 100 psi during contacting.

Flow of feedstock 10 may be discontinued and flow of turbine exhaust 70 may be decreased or diverted to conduct rejuvenation. A rejuvenation gas 45 comprising H2 is provided via rejuvenation system 40 and conduit 41. Rejuvenation gas 45 is optionally heated with convective heat in exchanger 42 and conducted to reactor tube(s) 23 via conduit 43, inlet manifold 14, and conduit 15. Rejuvenation gas 45 is contacted with the catalyst composition (not shown) inside reactor tube(s) 23 at about 400° C. to about 800° C. to remove at least a portion of coke material (not shown) from the catalyst composition. The outlet pressure of reactor tube(s) 23 is about 5 psia to about 250 psia during contacting with rejuvenation gas 45. At least 10 wt % of the incrementally deposited coke material is removed from the catalyst composition.

Rejuvenation effluent exits reactor tube(s) 23 and is conducted away to rejuvenation system 40 via conduit 30, outlet manifold 31 and conduit 44. Within rejuvenation system 40, the rejuvenation effluent comprising light hydrocarbon, unreacted hydrogen, and coke particulate is sent to a compression device (not shown) and then sent to a separation apparatus (also not shown) wherein a light hydrocarbon enriched gas and light hydrocarbon depleted gas are produced. The light hydrocarbon gas (not shown) is carried away for use, inter alia, as fuel gas. The light hydrocarbon depleted stream (also not shown) is combined with fresh rejuvenation gas 45 in rejuvenation system 40 and provided to the reactor tube(s) 23. Following sufficient coke removal, the flow of rejuvenation gas 45 is discontinued and providing feedstock 10 and increased flow of turbine exhaust 70 is resumed.

Flow of feedstock 10 may be discontinued and flow of turbine exhaust 70 may be decreased to conduct regeneration. A purge gas 54 is provided via regeneration system 50 and conduit 51. Flow of purge gas 54 is provided to purge any combustible gas, including feedstock and reactor product, from the reactor tube(s) 23 and related conduits and manifolds. Following purging, regeneration gas 53 comprising an oxidizing material, e.g., air, is provided via regeneration system 50 and conduit 51. Regeneration gas 53 is conducted to reactor tube(s) 23 via conduit 51, inlet manifold 14, and conduit 15. Regeneration gas 53 is contacted with the catalyst composition (not shown) inside reactor tube(s) 23 to remove at least a portion of coke material (not shown) from the catalyst composition by oxidation with the regeneration gas 53. Regeneration effluent exits reactor tube(s) 23 and is conducted away to regeneration system 50 via conduit 30, outlet manifold 31, and conduit 52. When sufficient coke has been removed, e.g., at least 10 wt % of coke has been removed or when no further oxidation is detected by low concentration of oxidation products such as CO or CO2 leaving the reactor tube(s) 23, the flow of regeneration gas 53 is discontinued. Flow of purge gas 54 is resumed to purge regeneration gas from the reactor tube(s) 23. Following purging, the flow of feedstock 10 and increased flow of turbine exhaust 70 is resumed.

Figure 3:
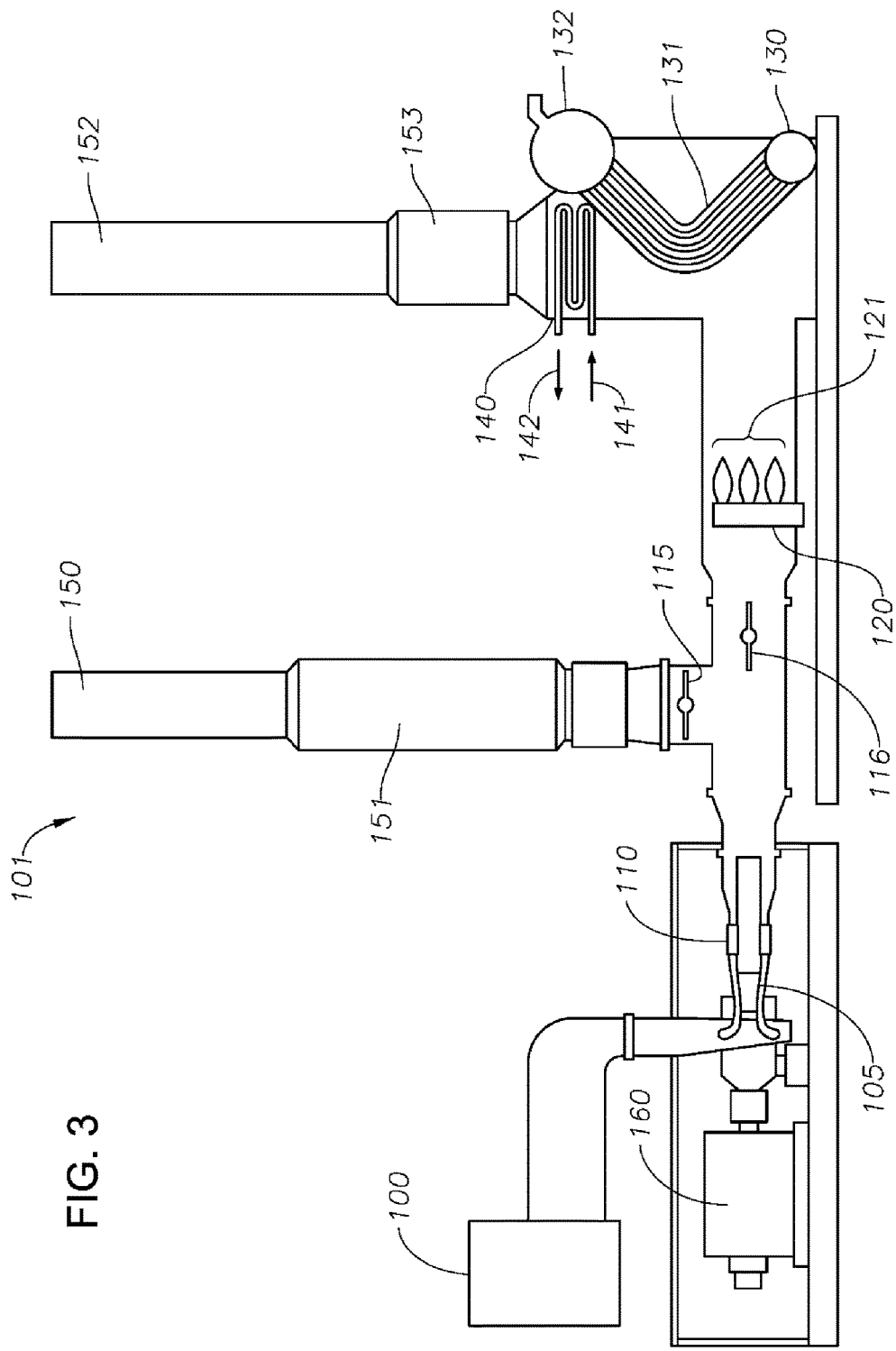
FIG. 3 illustrates an integrated conversion system and process.

Referring to FIG. 3, an integrated conversion system and process for generating power and converting acyclic C5 hydrocarbon to cyclic C5 hydrocarbon is illustrated. The conversion system 101 comprises a filter 100 which filters a gas stream comprising oxygen (air) that is conducted to a compressor 105. Compressed air is burned with fuel gas (not shown) in turbine 110. Expanding combustion gas inside turbine 110 produces turbine power and a turbine exhaust stream (not shown). Turbine power turns compressor 105 and electric generator 160 producing electric power. Combustion device 120 comprising duct burners 121 provides additional heat input to the turbine exhaust stream. Heat from turbine exhaust stream is transferred by convection to reactor tubes 131. A feedstock stream comprising acyclic C5 hydrocarbon (not shown) is conducted to reactor tubes 131 via inlet manifold 130. Feedstock is contacted with catalyst composition (not shown) in reactor tubes 131 and reactor effluent (also not shown) exits reactor tubes 131 via outlet manifold 132. Heat transfer means 140 comprising heat transfer exchanger tubes enables additional heat to be transferred by convection from turbine exhaust before the turbine exhaust exits stack 152 comprising an exhaust silencer 153.

Rejuvenation gas and/or regeneration gas 141 is heated in heat transfer means 140 and conducted to reactor tubes 131 via conduit 142. The amount of heat transfer by convection to reactor tubes 131 may be reduced by closing baffle 116 and opening of baffle 115, which redirects at least a portion of turbine exhaust away from reactor tubes 131 and through bypass stack 150 comprising silencer 151.

Example 2

A mixture with ~22% solids was prepared by mixing 8,800 g of DI water, 600 g of 50% NaOH solution, 26 g of 43% Sodium Aluminate solution, 730 g of n-propyl amine 100% solution, 20 g of ZSM-5 seed crystals, and 3,190 g of Sipernat-340 silica in a 5-gal pail container. The mixture was then charged into a 5-gal autoclave. The mixture had the following molar composition:

| | |
|---|---|
| $SiO_2/Al_2O_3$ | ~470 |
| $H_2O/SiO_2$ | ~10.7 |
| $OH/SiO_2$ | ~0.16 |
| $Na/SiO_2$ | ~0.16 |
| n-PA/Si | ~0.25. |

In the autoclave, the mixture was mixed at 350 rpm and reacted at 210° F. (99° C.) for 72 hours. The resulting reaction slurry was discharged and stored in a 5-gal pail container. The XRD pattern (not shown) of the as-synthesized material showed the typical pure phase of ZSM-5 topology. The SEM (not shown) of the as-synthesized material shows that the material was composed of a mixture of crystals with a size of 0.5-1 micron. The as-synthesized crystals had a $SiO_2/Al_2O_3$ molar ratio of ~467 and Na of ~0.25 wt %.

This material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. for 6 hours. After cooling, 0.29 wt % Ag was added via incipient wetness impregnation using an aqueous solution of silver nitrate. The sample was dried for four hours at 250° F. (120° C.). Subsequently, 0.44 wt % Pt was added via incipient wetness impregnation using an aqueous solution of tetraamine platinum hydroxide. The catalyst was dried in air at room temperature then at 250° F. (120° C.), and calcined in air for one hour at 610° F. (320° C.).

Example 3

The catalyst of Example 2 was tested under two reactor temperature profiles: a substantially isothermal temperature profile and an inverse temperature profile. The catalyst (0.5 g) was physically mixed with quartz (1.5 g, 60-80 mesh) and loaded into a ⅜" OD, 18" long stainless steel reactor. The catalyst bed was held in place with quartz wool and the reactor void space was loaded with coarse quartz particles. The catalyst was dried for 1 hour under He (100 mL/min, 30 psig, 250° C.) then reduced for 1 hour under H2 (200 mL/min, 30 psig, 500° C.). The catalyst was then tested for performance with a feed containing n-pentane, H2, and balance He.

The test conditions for maintaining an isothermal temperature profile were the following: 0.5 g ZSM-5(400:1)/ 0.4% Pt/0.2% Ag, 5 psia C5H12 at reactor inlet, 1:1 H2:C5 feed, and 60 psia total pressure with He balance, WHSV was 16.1 h−1, 600° C. bed temperature. The test conditions for maintaining an inverse temperature profile were the following: 0.5 g ZSM-5(400:1)/0.4% Pt/0.2% Ag, 5 psia C5H12 at reactor inlet, 1:1 H2:C5 feed, and 60 psia total pressure with He balance, WHSV was 4.0 h−1 for the gradient experiment and a linear temperature gradient of 500 to 600° C. was applied. The performance results of Example 3 are shown in FIGS. 4 and 5.

Figure 4:
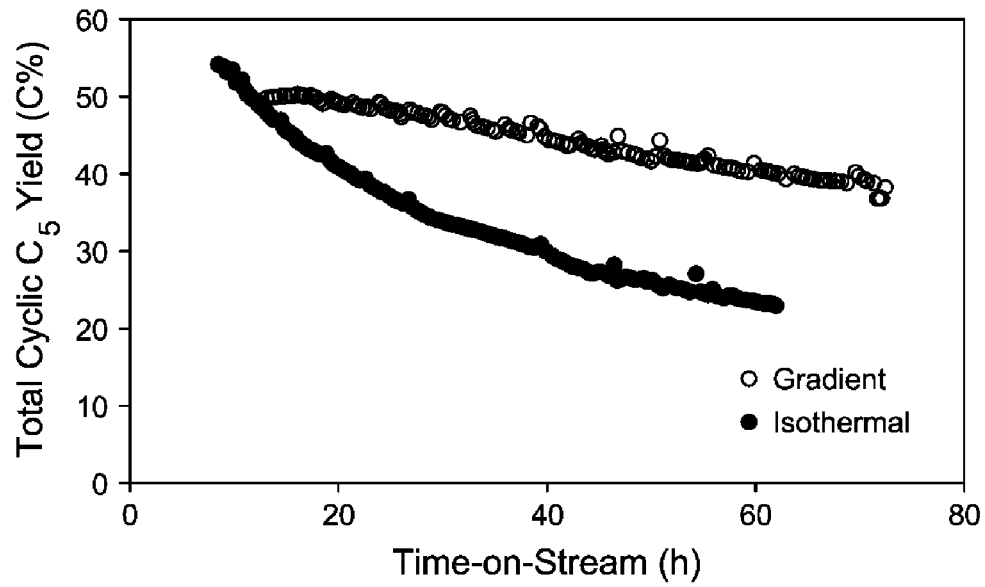
FIG. 4 illustrates the total carbon yield of cyclic C5 hydrocarbons against time on stream (T.O.S.) in Example 3 while maintaining an inverse temperature profile (500 to 600° C. over 6 inches) or an isothermal temperature profile (600° C. throughout the 6 inches).
Figure 5:
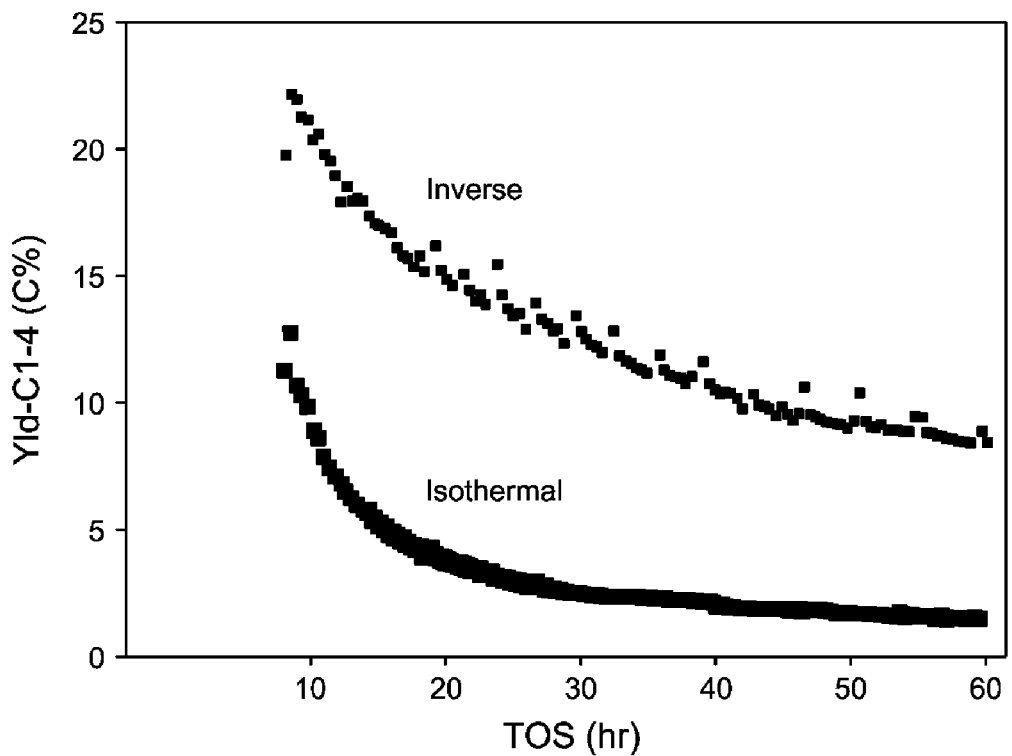
FIG. 5 illustrates the total carbon yield of C1-C4 hydrocarbons against T.O.S. in Example 3 while maintaining an inverse temperature profile (500 to 600° C. over 6 inches) or an isothermal temperature profile (600° C. throughout the 6 inches).

As shown in FIG. 4, a reactor operating with an inverse or gradient temperature profile (i.e., a lower temperature at the inlet and a higher temperature at the outlet), results in a catalyst having higher stability over that of a reactor operating isothermally at the same outlet temperature. Specifically, FIG. 4 shows that while the total cyclic C5 hydrocarbon yield for both temperature profiles was similar initially, the yield decreased to 43% of its original value over 53 hours in the reactor having an isothermal temperature profile. In contrast, the yield in an inverse temperature profile operating regime only decreased to 73% of its original value, and this decline in yield occurred over a longer timeframe of 57 hours. As shown in FIG. 5, a reactor operating isothermally can be beneficial over that operating with an inverse or gradient temperature profile when it is desired to minimize the yield of byproduct C1-C4 cracked hydrocarbon products.

Example 4

A mixture with ~22% solids was prepared by mixing 950 g of DI water, 53.5 g of 50% NaOH solution, 76.8 g of n-propyl amine 100% solution, 10 g of ZSM-5 seed crystals, and 336 g of Ultrasil PM™ Modified silica, and 4.4 g of Silver Nitrate in a 2-liter container. The mixture was then charged into a 2-liter autoclave. The mixture had the following molar composition:

| | |
|---|---|
| $SiO_2/Al_2O_3$ | >1000 |
| $H_2O/SiO_2$ | ~10.98 |
| $OH/SiO_2$ | ~0.17 |
| $Na/SiO_2$ | ~0.17 |
| n-PA/Si | ~0.25. |

In the autoclave, the mixture was mixed at 250 rpm and reacted at 230° F. (110° C.) for 72 hours. The resulting products were filtered and washed with deionized water then dried overnight at 250° F. The XRD pattern (not shown) of the as-synthesized material showed the typical pure phase of ZSM-5 topology. The SEM (not shown) of the as-synthesized material shows that the material was composed of a mixture of large crystals with a size of <1 micron. The resulting ZSM-5 crystals had a SiO2/Al2O3 molar ratio of >800, Na of ~0.28%, and Ag of 0.9 wt %.

This material was calcined for 6 hours in nitrogen at 482° C. After cooling, the sample was re-heated to 900° F. in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. for 6 hours. After cooling, 0.45 wt % Pt was added via incipient wetness impregnation using an aqueous solution of tetraamine platinum hydroxide. The catalyst was dried in air at room temperature then at 250° F., and calcined in air for three hours at 350° C. The catalyst powder was pressed (15 ton), crushed, and sieved to obtain 40-60 mesh particle size.

Example 5

Figure 6:
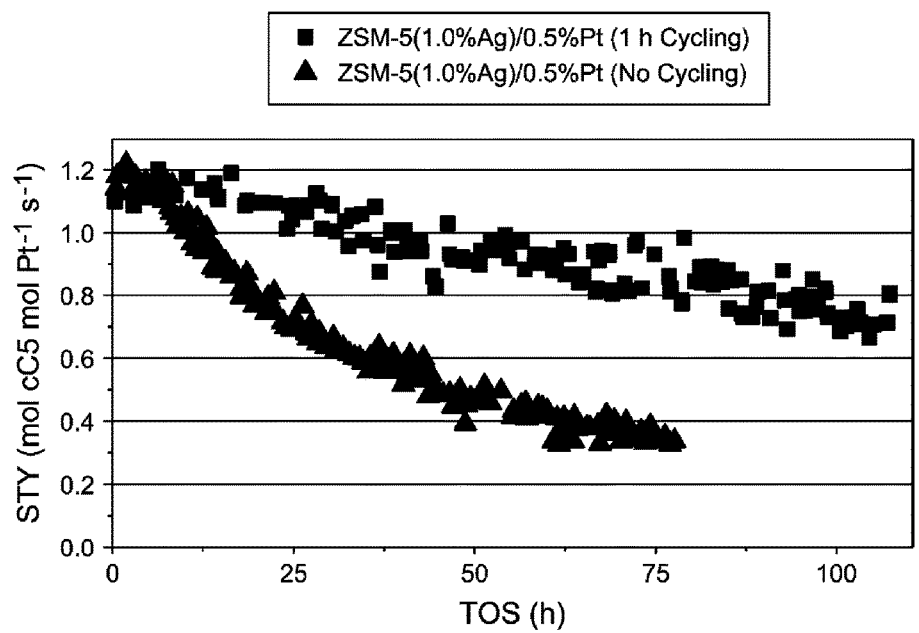
FIG. 6 illustrates the site-time-yield (STY) of cyclic C5 hydrocarbons (i.e., the mols of cC5/mol of Pt/second) against T.O.S. in Example 5 under a continuously-on-oil reactor operating strategy and an intermittent H2 rejuvenation reactor operating strategy.

The catalyst of Example 4 was tested under two reactor operating strategies: a continuously on-oil strategy and an intermittent H2 rejuvenation strategy. The catalyst (0.5 g) was physically mixed with quartz (1.5 g, 60-80 mesh) and loaded into a ⅜" OD, 18" long stainless steel reactor. The catalyst bed was held in place with quartz wool and the reactor void space was loaded with coarse quartz particles. The catalyst was dried for 1 hour under He (100 mL/min, 30 psig, 250° C.) then reduced for 1 hour under H2 (200 mL/min, 30 psig, 500° C.). The catalyst was then tested for performance with a feed containing n-pentane, H2, and balance He. The test conditions for a continuously on-oil operating strategy were the following: 0.5 g [0.96% Ag]—ZSM-5/0.5% Pt, 5.0 psia C5H12, 1:1 molar H2:C5, 14.7 WHSV, 45 psia total during the on-oil period. The test conditions for an intermittent H2 rejuvenation strategy were the following: the reactor was cycled for one hour on-oil and one hour on H2 rejuvenation at the conditions of 200 $cm^3$ $min^{-1}$ H2 at 600° C. and 45 psia of all H2; i.e., with no additional He. Performance results for both operating strategies are shown in FIG. 6 as the site-time-yield of cyclic C5's (i.e., the mols of cC5/mol of Pt/second). FIG. 6 demonstrates that the H2 rejuvenation is capable of improving catalyst capability over time to catalyze C5 hydrocarbon cyclization.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition element, or elements and vice versa.

The invention claimed is:

1. A process for converting acyclic C5 hydrocarbon to cyclic C5 hydrocarbon, wherein the process comprises:
    a) compressing a gas stream comprising oxygen;
    b) oxidizing fuel with the compressed gas stream to produce a hot gas stream;
    c) providing feedstock comprising acyclic C5 hydrocarbon;
    d) contacting the feedstock with catalyst composition in parallel reactor tubes while transferring heat by convection from the hot gas stream to the outer surface of the reactor tube walls; and
    e) obtaining reactor effluent comprising cyclic C5 hydrocarbon, wherein the cyclic C5 hydrocarbon comprises cyclopentadiene.

2. An integrated process for generating power and converting acyclic C5 hydrocarbon to cyclic C5 hydrocarbon, wherein the process comprises:
    a) compressing a gas stream comprising oxygen;
    b) burning fuel gas with the compressed gas stream in a turbine to produce turbine power and a turbine exhaust stream;
    c) providing feedstock comprising acyclic C5 hydrocarbon;
    d) contacting the feedstock with catalyst composition in parallel reactor tubes while transferring heat by convection from the turbine exhaust stream to the outer surface of the reactor tube wall; and e) obtaining reactor effluent comprising cyclic C5 hydrocarbon wherein, the cyclic C5 hydrocarbon comprises cyclopentadiene.

3. The process of claim 1, wherein the reactor tubes have an inverse temperature profile or an isothermal temperature profile.

4. The process of claim 1, wherein the feedstock and the hot gas stream flow in the same direction providing a heat flux near the inlet that is greater than the heat flux near the outlet of the reactor tubes.

5. The process of claim 1, further comprising burning additional fuel with unreacted oxygen in the hot gas stream to increase the temperature of the hot gas stream prior to said transferring heat by convection in step d).

6. The process of claim 1, wherein the contacting feedstock and catalyst composition is performed in the presence of $H_2$, $C_1$, $C_2$, $C_3$, and/or $C_4$ hydrocarbons.

7. The process of claim 1, further comprising promoting heat transfer to the catalyst composition by providing fins or contours on the inside and/or outside of the reactor tubes.

8. The process of claim 7, wherein the fins and/or the contours promote a heat flux near the inlet that is greater than the heat flux at the reactor tube outlet.

9. The process of claim 1, further comprising mixing feedstock and converted cyclic C5 hydrocarbon in the radial direction by providing mixing internals within the reactor tubes, wherein the mixing internals are positioned i) within a bed of the catalyst composition or ii) in portions of the reactor tube separating two or more zones of catalyst composition.

10. The process of claim 1, wherein contacting feedstock with the catalyst composition occurs at a temperature of about 450° C. to about 800° C.

11. The process of claim 1, wherein the reactor tubes have an outlet pressure of about 4 psia to about 50 psia during contacting feedstock with catalyst composition.

12. The process of claim 1, wherein the reactor tubes, during contacting feedstock with catalyst composition, have a pressure drop measured from reactor inlet to reactor outlet from about 1 psi to about 100 psi.

13. The process of claim 1, wherein the catalyst composition comprises platinum on ZSM-5, platinum on zeolite L, and/or platinum on silicate modified silica.

14. The process of claim 1, wherein the catalyst composition is an extrudate having a diameter of 2 mm to 20 mm.

15. The process of claim 1, wherein the catalyst composition cross section is shaped with one or more lobes and/or concave sections, and wherein the catalyst composition lobes and/or concave sections are spiraled or straight.

16. The process of claim 1, wherein the inside diameter of the reactor tubes is from about 20 mm to about 200 mm.

17. The process of claim 1, further comprising transferring an additional amount of heat by convection from the hot gas stream to rejuvenation gas, regeneration gas, the feedstock, the fuel, the gas stream comprising oxygen, and/or steam.

18. The process of claim 1, further comprising i) providing two or more pluralities of parallel reactor tube(s), the reactor tubes containing catalyst composition and ii) providing a rejuvenation gas or a regeneration gas to one or more reactor tube pluralities and providing feedstock comprising acyclic C5 hydrocarbons to a different one or more reactor tube pluralities.

19. The process of claim 1 further comprising:
a) discontinuing providing a feedstock comprising acyclic C5 hydrocarbons and reducing the amount of heat transferred by convection from the hot gas stream;
b) providing a rejuvenation gas comprising H2;
c) contacting the rejuvenation gas with the catalyst composition to remove at least a portion of coke material on the catalyst composition; and
d) discontinuing providing a rejuvenation gas and resuming providing a feedstock comprising acyclic C5 hydrocarbons and increasing the amount of heat transferred by convection from the hot gas stream.

20. The process of claim 1 further comprising:
a) discontinuing providing a feedstock comprising acyclic C5 hydrocarbons and reducing the amount of heat transferred by convection from the hot gas stream;
b) purging any combustible gas, including feedstock and reactor product, from the reactor tubes;
c) contacting a regeneration gas comprising an oxidizing material with the catalyst composition to remove by oxidation at least a portion of coke material on the catalyst composition;
d) purging regeneration gas from the reactor tubes; and
e) discontinuing purging with regeneration gas and resuming providing a feedstock comprising acyclic C5 hydrocarbons and increasing the amount of heat transferred by convection from the hot gas stream.

21. The process of claim 1, wherein the catalyst composition is formed into a structured catalyst shape.

22. The process of claim 1, further comprising providing the feedstock to at least one adiabatic reaction zone prior to the contacting of d).

23. The process of claim 1, wherein the oxidizing of b) is performed in a turbine, fuel cell, furnace, boiler, excess air burner, and/or fluidized bed, and wherein said fuel is selected from the group consisting of coal, fuel oil, hydrogen, methane, and mixtures thereof.

* * * * *